(12) United States Patent
Matoga et al.

(10) Patent No.: US 10,307,730 B2
(45) Date of Patent: Jun. 4, 2019

(54) METAL-ORGANIC FRAMEWORKS (MOFS), METHOD FOR THEIR PREPARATION AND THEIR APPLICATION

(71) Applicant: UNIWERSYTET JAGIELLONSKI, Cracow (PL)

(72) Inventors: Dariusz Matoga, Siepraw (PL); Kornel Roztocki, Jedlicze (PL)

(73) Assignee: UNIWERSYTET JAGIELLOŃSKI, Cracow (PL)

( * ) Notice: Subject to any disclaimer, the term of this patent is extended or adjusted under 35 U.S.C. 154(b) by 139 days.

(21) Appl. No.: 15/318,678

(22) PCT Filed: Jun. 16, 2015

(86) PCT No.: PCT/IB2015/054558
§ 371 (c)(1),
(2) Date: Dec. 14, 2016

(87) PCT Pub. No.: WO2015/193820
PCT Pub. Date: Dec. 23, 2015

(65) Prior Publication Data
US 2018/0161755 A1    Jun. 14, 2018

(30) Foreign Application Priority Data

Jun. 16, 2014 (PL) ........................ 408565

(51) Int. Cl.

| | |
|---|---|
| H01M 8/1018 | (2016.01) |
| B01J 20/22 | (2006.01) |
| B01J 31/02 | (2006.01) |
| C07F 3/00 | (2006.01) |
| H01M 10/056 | (2010.01) |
| B01J 20/30 | (2006.01) |
| C07F 1/00 | (2006.01) |
| C07F 7/00 | (2006.01) |
| C07F 15/04 | (2006.01) |
| C07F 15/06 | (2006.01) |
| H01M 10/052 | (2010.01) |
| H01M 10/054 | (2010.01) |

(52) U.S. Cl.
CPC ......... *B01J 20/226* (2013.01); *B01J 20/3085* (2013.01); *B01J 31/0235* (2013.01); *C07F 1/005* (2013.01); *C07F 3/003* (2013.01); *C07F 7/003* (2013.01); *C07F 15/045* (2013.01); *C07F 15/065* (2013.01); *H01M 8/1018* (2013.01); *H01M 10/056* (2013.01); *H01M 10/052* (2013.01); *H01M 10/054* (2013.01); *H01M 2300/002* (2013.01); *H01M 2300/0025* (2013.01)

(58) Field of Classification Search
None
See application file for complete search history.

(56) References Cited

PUBLICATIONS

Hu et al., Cryst. Eng. Comm., 15(45), 2013, 9553-9561. (Year: 2013).*
Lu et al., Polyhedron, 83, 2014, 108-115 (Year: 2014).*
International Search Report and Written Opinion issued in corresponding International Patent Application No. PCT/IB2015/054558 dated Oct. 2, 2015 (9 pages).
Lu et al., "A series of two-dimensional coordination polymer crystal materials based on two flexible bis-pyridyl-bis-amide ligands with fluorescent sensing activities and photocatalytic properties," Polyhedron, vol. 83, 2014, pp. 108-115.
Hu et al., "Structure diversities of ten entangled coordination polymers assembled from reactions of Co(II) or Ni(II) salts with 5-(pyridin-4-yl)isophthalic acid in the absence or presence of auxiliary N-donor ligands," CrystEngComm, vol. 15, No. 45, 2013, pp. 9553-9561.

* cited by examiner

*Primary Examiner* — Clinton A Brooks
*Assistant Examiner* — Kofi Adzamli
(74) *Attorney, Agent, or Firm* — Kilyk & Bowersox, P.L.L.C.

(57) ABSTRACT

Coordination polymers of MOF type, comprising a repeating unit of the general formula $[M_2(dcx)_2L_2]$, wherein M represents a metal cation ($M^{2+}$), dcx represents an anion of a dicarboxylic acid and L represents a neutral molecule of hydrazone. A method for preparation of coordination polymers of MOF type, wherein in the first step a compound of aldehyde or ketone group is condensed with a hydrazide, and in the second step the condensation product is reacted using a metal compound and a dicarboxylic acid. An application of coordination polymers of MOF type for the detection, capturing, separation, or storage of molecules, for the fabrication of ionic conductors, for the construction of batteries and fuel cells, as well as drug carriers.

26 Claims, 3 Drawing Sheets

Figure 1:
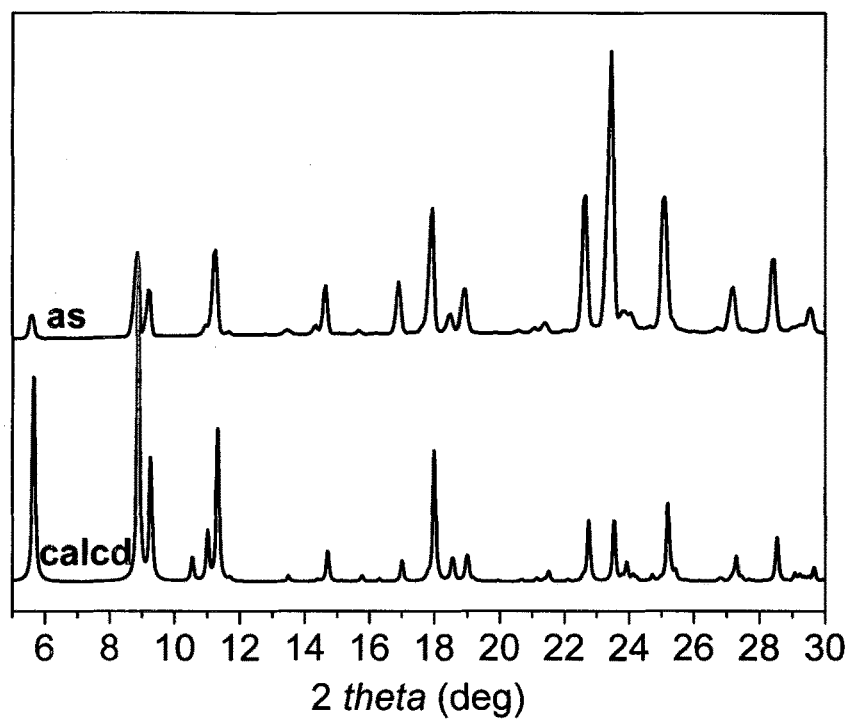

METAL-ORGANIC FRAMEWORKS (MOFS), METHOD FOR THEIR PREPARATION AND THEIR APPLICATION

The present invention relates to metal-organic frameworks (MOFs) of the formula $[M_2(dcx)_2L_2]$ containing dicarboxylates (dcx) and hydrazones (L), method for their preparation and their application.

In recent years the design and fabrication of metal-organic frameworks (MOF) has become one of the most intensively developing areas of materials chemistry and nanotechnology. The wide range of their practical application mainly results from the large inner surface and high flexibility, as well as high mechanical strength and thermal resistance. These characteristics provide these materials with the ability to adsorb different "guest" molecules, which is reflected in multiple applications of MOF materials including the storage of hydrogen and other gases, molecular identification, separation of mixtures (by selective sorption), catalysis, synthesis and adsorption of drugs. Because of the enormous variety of organic ligands, allowing for the control of network geometry, it is possible to design a product with unique properties based on the available reactants. Such metal-organic systems are described for example in U.S. Pat. No. 7,119,219, concerning the preparation of metal-organic network from a metal salt and a bidentate organic ligand. Another example of the preparation of a metal-organic network is the reaction of metal ions with one or more organic ligands, as disclosed in description EP0790253. Metal-organic networks can be obtained electrochemically, as disclosed in description U.S. Pat. No. 8,163,949.

The article Cooperative Effect of Unsheltered Amide Groups on CO2 Adsorption Inside Open-Ended Channels of a Zinc(II)-Organic Framework published in Inorg. Chem. 2013, 52, 3962-3968 describes for example a network comprising a zinc metalloligand with terephthalate groups.

Metal-organic frameworks (MOFs) according to the present invention comprise a repeating unit of the general formula $[M_2(dcx)_2L_2]$, wherein M is a metal cation ($M^{2+}$), dcx is an anion of a dicarboxylic acid, and L is a neutral molecule of hydrazone. Metal cation belongs to the group comprising: $Zn^{2+}$, $Cd^{2+}$, $Cu^{2+}$, $Mn^{2+}$, $Co^{2+}$, $Ni^{2+}$. The ligand dcx is an anion of carboxylic acid selected from 1,4-benzenedicarboxylic acid (formula 1), substituted 1,4-benzenedicarboxylic acid (formula 2), 1,4-cyclohexanedicarboxylic acid (formula 3), 2,6-naphthalenedicarboxylic acid (formula 4), biphenyl-4,4'-dicarboxylic acid (formula 5), thiophene-2,5-dicarboxylic acid (formula 6), and 2,5-dihydroxyterephthtalic acid (formula 7), where X is selected from $NH_2$, Br, $NO_2$, OH.

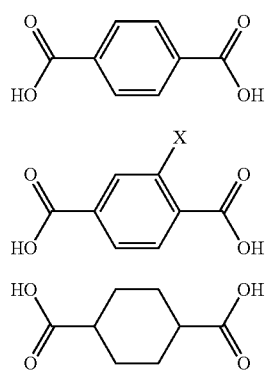

Hydrazone L is selected from compounds of the formulas 8, 9 or 10, wherein A, D, X, Z independently represent a nitrogen (N) atom, or a carbon atom with the amine substituent (C—$NH_2$), or a carbon atom with a hydrogen atom (CH), and wherein R represents a hydrogen atom, a $C_1$-$C_6$ alkyl or aryl group.

A method for preparation of metal-organic frameworks (MOFs) of the formula $[M_2(dcx)_2L_2]$ according to the present invention consists of two steps. The first step comprises a synthesis of hydrazone, wherein a compound from the group of aldehydes or ketones, selected from the compounds of the formulas 11, 12 or 13,

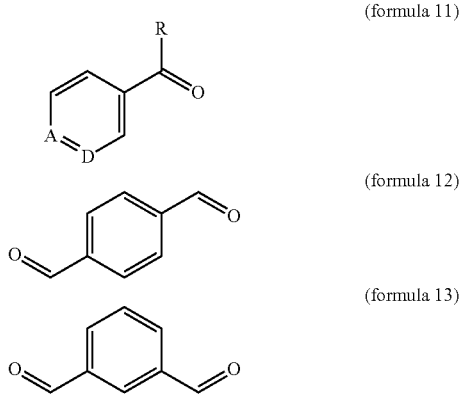

(formula 11)

(formula 12)

(formula 13)

wherein A and D independently represent a nitrogen (N) atom, a carbon atom with an amine substituent (C—$NH_2$), or a carbon atom with a hydrogen atom (CH), and R represents a hydrogen atom, a $C_1$-$C_6$ alkyl or aryl group is condensed with a hydrazide of the formula 14, wherein X and Z independently represent a nitrogen (N) atom, a carbon atom with an amine substituent (C—$NH_2$), or a carbon atom with a hydrogen atom (CH).

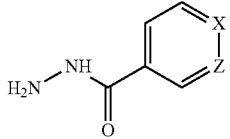

(formula 14)

The condensation reaction is conducted at a 1:1 molar ratio of carbonyl to hydrazide group or with a stoichiometric excess of one of the reactants. The reaction is conducted by mechanochemical means (without or with a small participation of a solvent) or in a solvent selected from $C_1$-$C_8$ alcohols, aqueous alcoholic solutions, N,N'-dimethylformamide (DMF), or N,N'-diethylformamide (DEF), preferably in ethanol or in an aqueous alcoholic solution. The product of the first step is hydrazone L of the formula 8, 9 or 10, in its ketone or enol form, neutral or deprotonated.

In the second step the condensation product, hydrazone L, is reacted with a compound selected from $M(NO_3)_2$, $M(ClO_4)_2$, $M(SO_4)_2$, or $M(CH_3COO)_2$, $MCl_2$ using a dicarboxylic acid selected from the acids of the formulas 1-7. The reaction is conducted at a 1:1:1 molar ratio of metal to dicarboxylic acid and hydrazone L or with a stoichiometric excess or deficiency of one of the reactants.

Both steps of the synthesis are conducted within a temperature range from −20° C. to 150° C., preferably from 60 do 130° C. and under autogenous pressure, in a closed vessel.

The application of coordination polymers of MOF type according to the present invention comprise the detection, capturing, separation or storage of molecules such as hydrogen, carbon dioxide, carbon monoxide, alcohols, water, hydrocarbons, fabrication of ionic conductors, including those containing $H^+$, $Li^+$, $Na^+$, $K^+$, $NH_4^+$, construction of batteries and fuel cells, as well as drug carriers.

The advantage of a metal-organic framework (MOF) of the formula $[M_2(dcx)_2L_2]$ is a combination of two types of ligands (dcx and L), which allowed for the compensation of the charge of metal ions ($M^{2+}$) with anions of dicarboxylic acids and the introduction of two different functional groups (C═O and N—H) in the form of a neutral hydrazone linker into the framework. These moieties may play a respective role of an acceptor or a donor of hydrogen bond, thereby creating the possibility of a selective interaction with potential molecules-guests and a dynamic behavior of the framework in case of interpenetration and interaction of interpenetrating frameworks using hydrogen bonds. Furthermore, hydrazide-hydrazones L introduced into the network can be subject to both keto-enol tautomerism and deprotonation, which can be used in case of further postsynthetic modifications of the network with ions introduced e.g. mechanochemically.

The invention has been described using the following embodiment.

EXAMPLE 1

Synthesis of $[M_2(dcx)_2L_2]$·G (product 1),
wherein $M^{2+}$=$Zn^{2+}$; dcx=anion of 1,4-benzenedicarboxylic acid; L=hydrazone of the formula 8, wherein A=N; D=CH; X=N; Z=CH; R=H; G=1DMF·1$H_2O$ Step 1: Synthesis of hydrazone L:

Isonicotinic acid hydrazide (686 mg; 5.00 mmol) was dissolved in 20 $cm^3$ of ethanol. 4-picolinic aldehyde (0.471 $cm^3$; 5.00 mmol) was added and the mixture was heated to reflux for 20 min. Subsequently the solution was left to cool and crystallize the product. After the crystallization the precipitate was filtered, and the filtrate was concentrated and left in ice bath until the crystallization of a further product fraction. The second crystallized fraction was filtered. The fractions were combined and air-dried. Yield: 1.02 g (90%). The synthesis and the X-ray structure of this hydrazone were described in the literature (W.-X. Ni, M. Li, X.-P. Zhou, Z. Li, X.-C. Huang, D. Li Chem. Commun. 2007, 3479).

The compound was identified spectrally based on the selected bands:

FT-IR (ATR, $cm^{-1}$): ν(C═O)$_L$ 1683, ν(NH) 3190.

Step 2: Hydrazone L (453 mg; 2.00 mmol), 1,4-benzenedicarboxylic acid (332 mg; 2.00 mmol) and $Zn(NO_3)_2$ were dissolved in 162 $cm^3$ of N,N'-dimethylformamide (DMF) and 18 $cm^3$ of water. The sealed vessel was heated at 70° C. for 48 hours to yield a fine-crystalline yellow product (420 mg). The product was washed with DMF and dried in a vacuum oven (30 min, 60° C., 500 mbar). Yield: 42%.

The product was identified using elemental, spectral, crystallographic, diffractometric and thermogravimetric analysis:

Elemental analysis: Measured: N, 12.58; C, 49.80; H, 3.91. Calculated for $C_{43}H_{37}N_9O_{12}Zn_2$: N, 12.57; C, 51.51; H, 3.72%.

FT-IR (ATR, $cm^{-1}$): ν(COO)$_{as}$ 1580, ν(COO)$_s$ 1392, ν(C═O)$_{DMF}$ 1661, ν(C═O)$_L$ 1680, ν(NH) 3222.

Crystallographic data (SCXRD): orthorhombic system, space group Iabc, a=15.1123(3), b=9.9069(3), c=31.2591(6) Å, V=9404.0(3) Å$^3$, T=293(2) K, Z=8, $D_c$=1.403 Mg m$^{-3}$, μ=1.082 mm$^{-1}$, 61329 measured reflections, 5813 independent reflections, 4390 observed reflections [I>2σ(I)]. $R_1$=0.0724; $wR_2$=0.1918 [for 4390 observed reflections].

FIG. 1. PXRD powder diffraction pattern registered for product 1 (as). For comparison, a powder diffraction pattern calculated based on a single crystal SCXRD (calcd).

Figure 2:
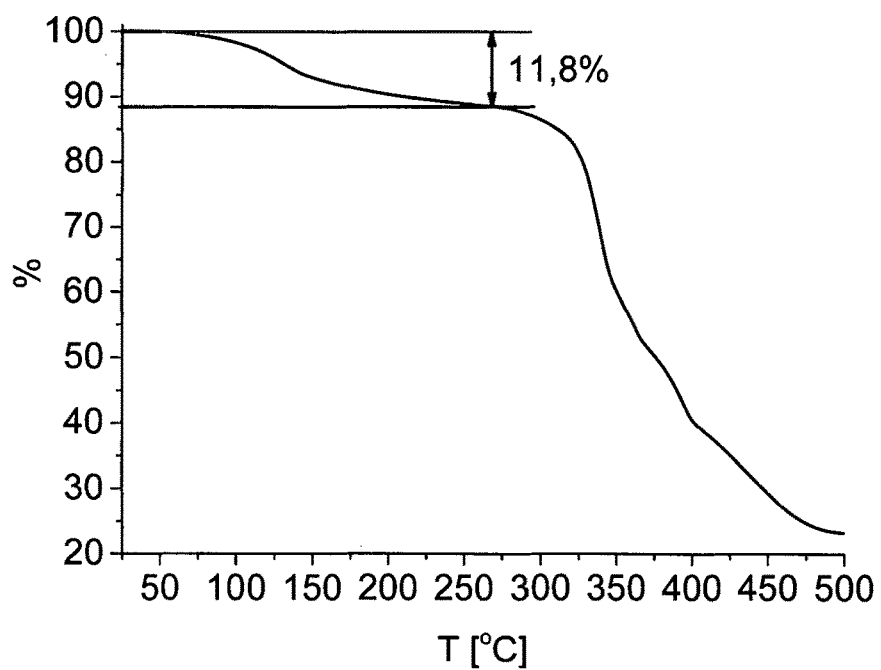

FIG. 2. Thermogravimetric curve for product 1.

Figure 3:
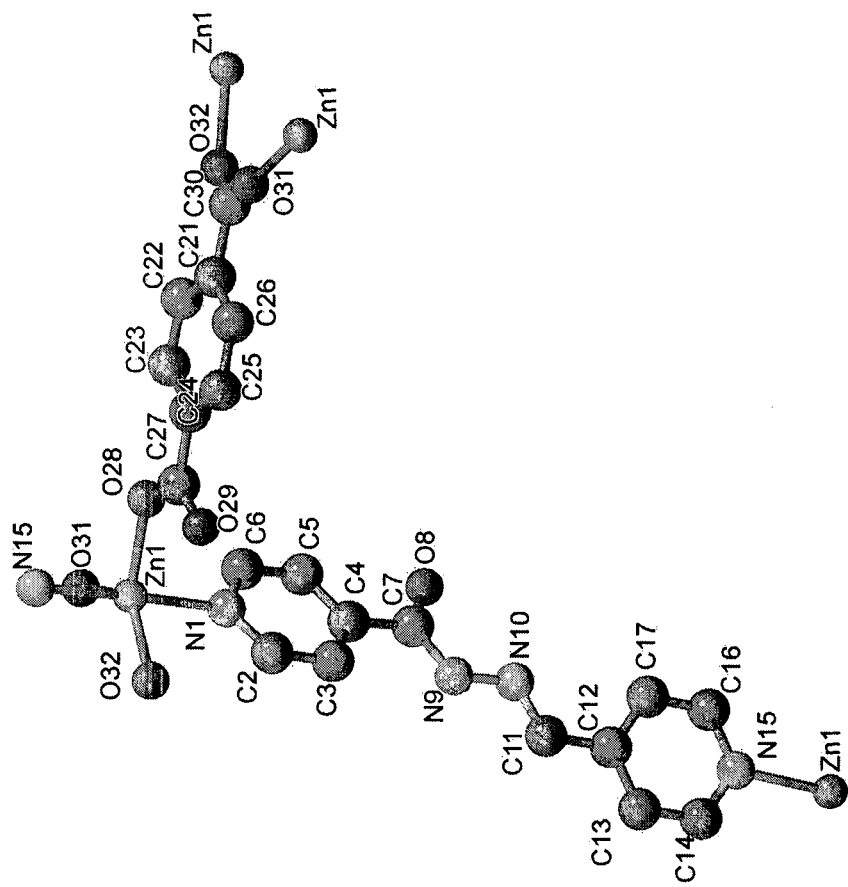
Figure 4:
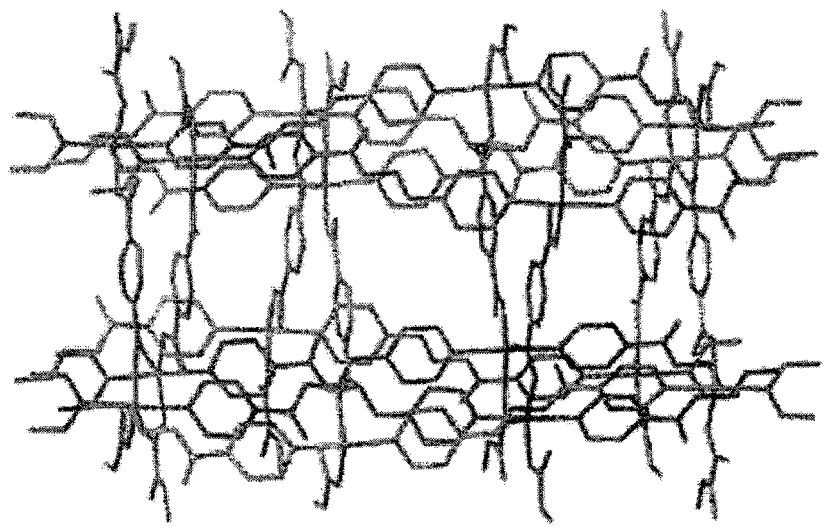
Figure 5:
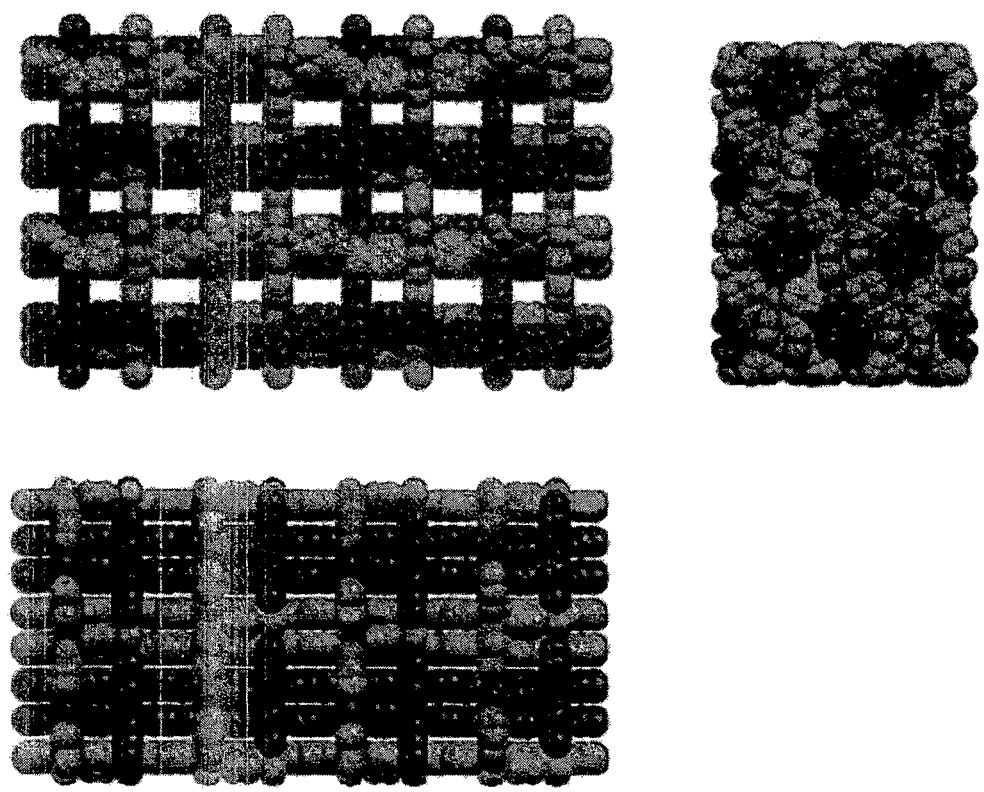

Spatial structure of the obtained product 1 was illustrated in figures: FIG. 3, FIG. 4 and FIG. 5.

FIG. 3. Fragment of the structure of product 1 illustrating the surrounding of Zn atoms (guest molecules and hydrogen atoms were skipped).

FIG. 4. Fragment of the structure of product 1 demonstrating a double interpenetration of pillared-layered network (blue and orange) with $Zn_2$ nodes-clusters forming layers with anions of a dicarboxylic acid dcx and hydrazone L, as a linker-pillar "supporting" the layers (guest molecules and hydrogen atoms were omitted).

FIG. 5. Orthographic projection of the structure of product 1, illustrating the presence of one-dimensional channels, the double interpenetration of the network and the pillared-layered structure (guest molecules and hydrogen atoms were omitted).

EXAMPLE 2

Synthesis of $[M_2(dcx)_2L_2]\cdot G$ (product 2),
wherein $M^{2+}=Zn^{2+}$; dcx=anion of 1,3-benzenedicarboxylic acid (formula XX below, X1=H);
L=hydrazone of the formula 8, wherein A=N; D=CH; X=N; Z=CH; R=H; G=2DMF Step 1: Synthesis of hydrazone L:
Isonicotinic acid hydrazide (686 mg; 5.00 mmol) was dissolved in 20 cm³ of ethanol. 4-picolinic aldehyde (0.471 cm³; 5.00 mmol) was added and the mixture was heated to reflux for 20 min. Subsequently the solution was left to cool and crystallize the product. After the crystallization the precipitate was filtered, and the filtrate was concentrated and left in ice bath until the crystallization of a further product fraction. The second crystallized fraction was filtered. The fractions were combined and air-dried. Yield: 1.02 g (90%). The synthesis and the X-ray structure of this hydrazone were described in the literature (W.-X. Ni, M. Li, X.-P. Zhou, Z. Li, X.-C. Huang, D. Li *Chem. Commun.* 2007, 3479).

The compound was identified spectrally based on the selected bands:
FT-IR (ATR, cm⁻¹): $\nu(C{=}O)_L$ 1683, $\nu(NH)$ 3190.

Step 2: Hydrazone L (36 mg; 0.16 mmol), 1,3-benzenedicarboxylic acid (27 mg; 0.16 mmol) and $Zn(NO_3)_2$ (62 mg; 0.16 mmol) were dissolved in 16.2 cm³ of N,N'-dimethylformamide (DMF) and 1.8 cm³ of water. The sealed vessel was heated at 60° C. for 70 hours to yield a fine-crystalline yellow product (20 mg). The product was washed with DMF and dried in a vacuum oven (30 min, 60° C., 500 mbar). Yield: 12%.

The product was identified using elemental, spectral, crystallographic, diffractometric and thermogravimetric analysis:
Elemental analysis: Measured: N, 13.21; C, 52.06; H, 4.19. Calculated for $C_{46}H_{44}N_{10}O_{12}Zn_2$: N, 13.22; C, 52.14; H, 4.19%.
FT-IR (ATR, cm⁻¹): $\nu(CO)_{as}$ 1557, $\nu(COO)_s$ 1394, $\nu(C{=}O)_{DMF}$ 1685, $\nu(C{=}O)_L$ 1675, $\nu(NH)$ 3208.

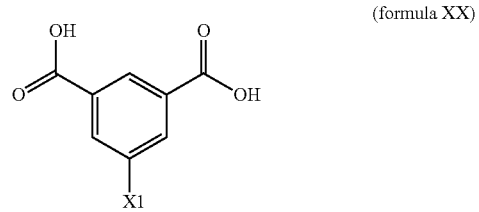

(formula XX)

X1 = H, NH₂, Br, NO₂, OCH₃, CH₃, OH

The invention claimed is:
1. A coordination polymer of MOF type, said coordination polymer comprises a repeating unit of the general formula $[M_2(dcx)_2L_2]$, wherein
M represents a metal cation ($M^{2+}$);
dcx represents an anion of a dicarboxylic acid;
L represents a neutral molecule of hydrazone having two different functional groups C=O and N—H.
2. The coordination polymer of MOF type according to claim 1, wherein the metal cation is $Zn^{2+}$, $Cd^{2+}$, $Cu^{2+}$, $Mn^{2+}$, $Co^{2+}$, or $Ni^{2+}$.
3. The coordination polymer of MOF type according to claim 1, wherein dcx is an anion of an acid that is 1,4-benzenedicarboxylic acid (formula 1), substituted 1,4-benzenedicarboxylic acid (formula 2), 1,4-cyclohexanedicarboxylic acid (formula 3), 2,6-naphthalenedicarboxylic acid (formula 4), biphenyl-4,4'-dicarboxylic acid (formula 5), thiophene-2,5-dicarboxylic acid (formula 6), or 2,5-dihydroxyterephthtalic acid (formula 7).
4. The coordination polymer of MOF type according to claim 1, wherein the hydrazone L is a compound of formula 8, 9 or 10:

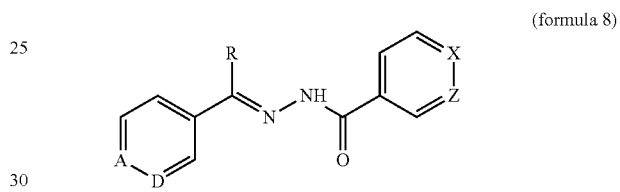

(formula 8)

(formula 9)

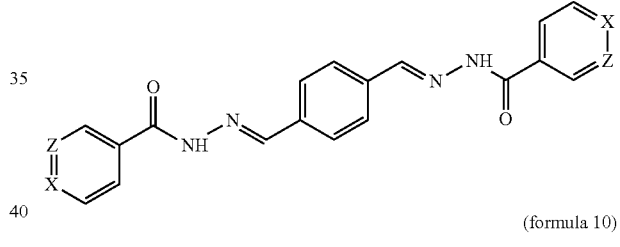

(formula 10)

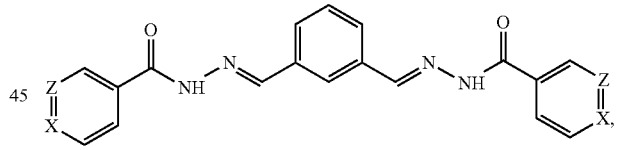

wherein A, D, X, Z independently represent a nitrogen (N) atom, or a carbon atom with an amine substituent (C—$NH_7$), or a carbon atom with a hydrogen atom (CH), and wherein R represents a hydrogen atom, a $C_1$-$C_6$ alkyl or aryl group.
5. The coordination polymer of MOF type according to claim 1, wherein the coordination polymer further comprises one or more types of guest molecules.
6. The coordination polymer of MOF type according to claim 5, wherein the guest molecules are molecules of a solvent.
7. The coordination polymer of MOF type according to claim 6, wherein the molecules of the solvent is water, N,N'-dimethylformamide, N,N'-diethylformamide, or a $C_1$-$C_8$ alcohol.
8. The coordination polymer of MOF type according to claim 5, wherein the guest molecules are gas molecules.
9. The coordination polymer of MOF type according to claim 8, wherein the gas molecules are $N_2$, $H_2$, $CO_2$, CO, Ar, NO, or $NO_2$.

10. The coordination polymer of MOF type according to claim 8, wherein the gas molecules are $C_1$-$C_6$ alkanes, $C_2$-$C_6$ alkenes, $C_2$-$C_6$ alkynes, $C_6$-$C_8$ arenes, or $C_1$-$C_8$ alcohols.

11. The coordination polymer of MOF type according to claim 1, wherein said coordination polymer is in the absence of guest molecules.

12. A method for preparation of the coordination polymer of MOF type of claim 1, said method comprising in a first step forming a hydrazone L, a compound of aldehyde or ketone group that is condensed with a hydrazide to form a condensation product.

13. The method according to claim 12, further comprising in a second step reacting the condensation product with a metal compound and a dicarboxylic acid.

14. The method according to claim 13, wherein the metal compound is $M(NO_3)_2$, $M(ClO_4)_2$, $M(SO_4)_2$, $M(CH_3COO)_2$ or $MCl_2$.

15. The method according to claim 13, wherein the dicarboxylic acid is 1,4-benzenedicarboxylic acid (formula 1), substituted 1,4-benzenedicarboxylic acid (formula 2), 1,4-cyclohexanedicarboxylic acid (formula 3), 2,6-naphthalenedicarboxylic acid (formula 4), biphenyl-4,4'-dicarboxylic acid (formula 5), thiophene-2,5-dicarboxylic acid (formula 6), or 2,5-dihydroxyterephthtalic acid (formula 7).

16. The method according to claim 12, wherein the compound of aldehyde or ketone group is a compound of formula 11, 12 or 13:

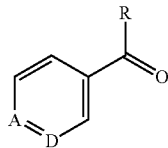

(formula 11)

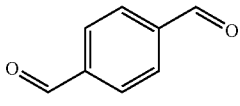

(formula 12)

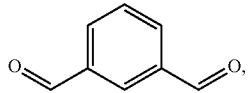

(formula 13)

wherein A and D independently represent a nitrogen (N) atom, a carbon atom with an amine substituent (C—$NH_2$), or a carbon atom with a hydrogen atom (CH), and R represents a hydrogen atom, a $C_1$-$C_6$ alkyl or aryl group condensed with a hydrazide.

17. The method according to claim 12, wherein the hydrazide is a compound of formula 14:

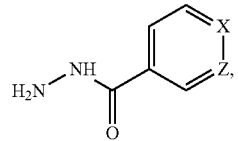

(formula 14)

wherein X and Z independently represent a nitrogen (N) atom, a carbon atom with an amine substituent (C—$NH_2$), or a carbon atom with a hydrogen atom (CH).

18. The method according to claim 12, wherein the condensation reaction is conducted by mechanochemical means.

19. The method according to claim 18, wherein the condensation reaction is conducted with the addition of 1-2 drops of sulfuric (VI) acid.

20. The method according to claim 12, wherein the condensation reaction is conducted in a solvent.

21. The method according to claim 20, wherein the solvent is $C_1$-$C_8$ alcohol, an aqueous alcoholic solution, N,N'-dimethylformamide (DMF), or N,N'-diethylformamide (DEF).

22. The method according to claim 12, wherein the first step is conducted within a temperature range of from −20° C. to 150° C.

23. The method according to claim 12, wherein the first step is conducted under autogenous pressure, in a closed vessel.

24. An application of coordination polymers of MOF type of the general formula $[M_2(dcx)_2L_2]$ according to claim 1, characterized in that the compounds are used for the detection, capturing, separation or storage of molecules, for the fabrication of ionic conductors, for the construction of batteries and fuel cells, as well as drug carriers.

25. An application according to claim 24, characterized in that the molecules are selected from water, carbon dioxide, carbon monoxide, alcohols, water, hydrocarbons.

26. An application according to claim 24, characterized in that the ionic conductors comprise ions selected from $H^+$, $Li^+$, $Na^+$, $IC$, $NH_4^+$.

* * * * *

UNITED STATES PATENT AND TRADEMARK OFFICE
CERTIFICATE OF CORRECTION

PATENT NO. : 10,307,730 B2
APPLICATION NO. : 15/318678
DATED : June 4, 2019
INVENTOR(S) : Matoga et al.

It is certified that error appears in the above-identified patent and that said Letters Patent is hereby corrected as shown below:

In the Claims

Claim 4, Column 6, Line 50, "$C-NH_7$" should read -- $C-NH_2$ --

Signed and Sealed this
Twenty-seventh Day of August, 2019

Andrei Iancu
*Director of the United States Patent and Trademark Office*